(12) United States Patent
Christensen

(10) Patent No.: US 8,691,050 B2
(45) Date of Patent: Apr. 8, 2014

(54) METHODS AND DEVICES FOR CONTINUOUS TRANSFER OF PARTICULATE AND/OR FIBROUS MATERIAL BETWEEN TWO ZONES WITH DIFFERENT TEMPERATURES AND PRESSURES

(76) Inventor: Børge Holm Christensen, Ålsgårde (DK)

( * ) Notice: Subject to any disclaimer, the term of this patent is extended or adjusted under 35 U.S.C. 154(b) by 63 days.

(21) Appl. No.: 13/130,748

(22) PCT Filed: Nov. 23, 2009

(86) PCT No.: PCT/IB2009/007537
§ 371 (c)(1),
(2), (4) Date: Aug. 11, 2011

(87) PCT Pub. No.: WO2010/058285
PCT Pub. Date: May 27, 2010

(65) Prior Publication Data
US 2011/0308141 A1    Dec. 22, 2011

Related U.S. Application Data

(60) Provisional application No. 61/116,663, filed on Nov. 21, 2008.

(30) Foreign Application Priority Data

Nov. 21, 2008   (DK) ................................ 2008 01641

(51) Int. Cl.
| | | |
|---|---|---|
| *D21B 1/22* | (2006.01) | |
| *B01J 8/08* | (2006.01) | |
| *B65G 53/08* | (2006.01) | |
| *C12P 7/10* | (2006.01) | |

(52) U.S. Cl.
USPC ................. 162/56; 162/14; 162/18; 162/23; 162/52; 422/233; 414/218; 414/805; 435/165

(58) Field of Classification Search
CPC .............. D21B 1/22; D21B 1/26; D21C 7/06; B01J 8/08; B01J 8/008; B01J 8/0015; B01J 8/002; B01J 8/0045; C01L 1/00; B65G 53/08; B65G 53/48; C21P 7/10
USPC ...................... 162/18, 23, 52, 56, 14; 241/28; 414/217–220, 805; 127/37; 435/161, 435/163, 165; 422/232, 233
See application file for complete search history.

(56) References Cited

U.S. PATENT DOCUMENTS

| | | | | |
|---|---|---|---|---|
| 3,841,465 | A * | 10/1974 | Miller et al. ................... | 241/247 |
| 4,121,967 | A | 10/1978 | Reinhall et al. | |
| 4,274,786 | A * | 6/1981 | Svensson et al. ............. | 414/218 |
| 4,881,862 | A * | 11/1989 | Dick ............................ | 414/218 |
| 6,145,766 | A | 11/2000 | Mraz et al. | |
| 7,976,259 | B2 * | 7/2011 | Craig et al. ................... | 414/218 |
| 2004/0060673 | A1 | 4/2004 | Phillips et al. | |
| 2005/0011622 | A1 | 1/2005 | Sabourin | |

FOREIGN PATENT DOCUMENTS

| | | |
|---|---|---|
| DE | 4420976 B1 | 12/1995 |
| EP | 0172135 A3 | 2/1986 |
| EP | 0406225 A2 | 1/1991 |
| EP | 0858880 A1 | 8/1998 |

OTHER PUBLICATIONS

International search report and written opinion for PCT/IB2009/007537.
First office action and reply in corresponding EP application 09768232.2.

* cited by examiner

*Primary Examiner* — Eric Hug

(57) ABSTRACT

Continuous transfer of particulate material into pressurized steam reactors is provided by "flow feeder" methods and devices. Material such as lignocellulosic biomass feedstocks are compacted into a "low density" plug, <700 kg/m3, which provides a dynamic seal against pressurized steam through exploitation of a steam condensation zone. The rate at which the steam condensation zone moves into the "low density" plug is offset by the rate at which compacted material is fed into the pressurized reactor. Preferred devices compact material within a flow feeder chamber by use of a loading device that works against counter-pressure provided by an unloading device. Compacted material is actively disintegrated and fed into the reactor by the unloading device. In preferred embodiments, compacted material is fed in a steady-state operation in which the interface between the steam condensation zone and the low pressure inlet zone remains stationary within the flow feeder chamber.

30 Claims, 2 Drawing Sheets

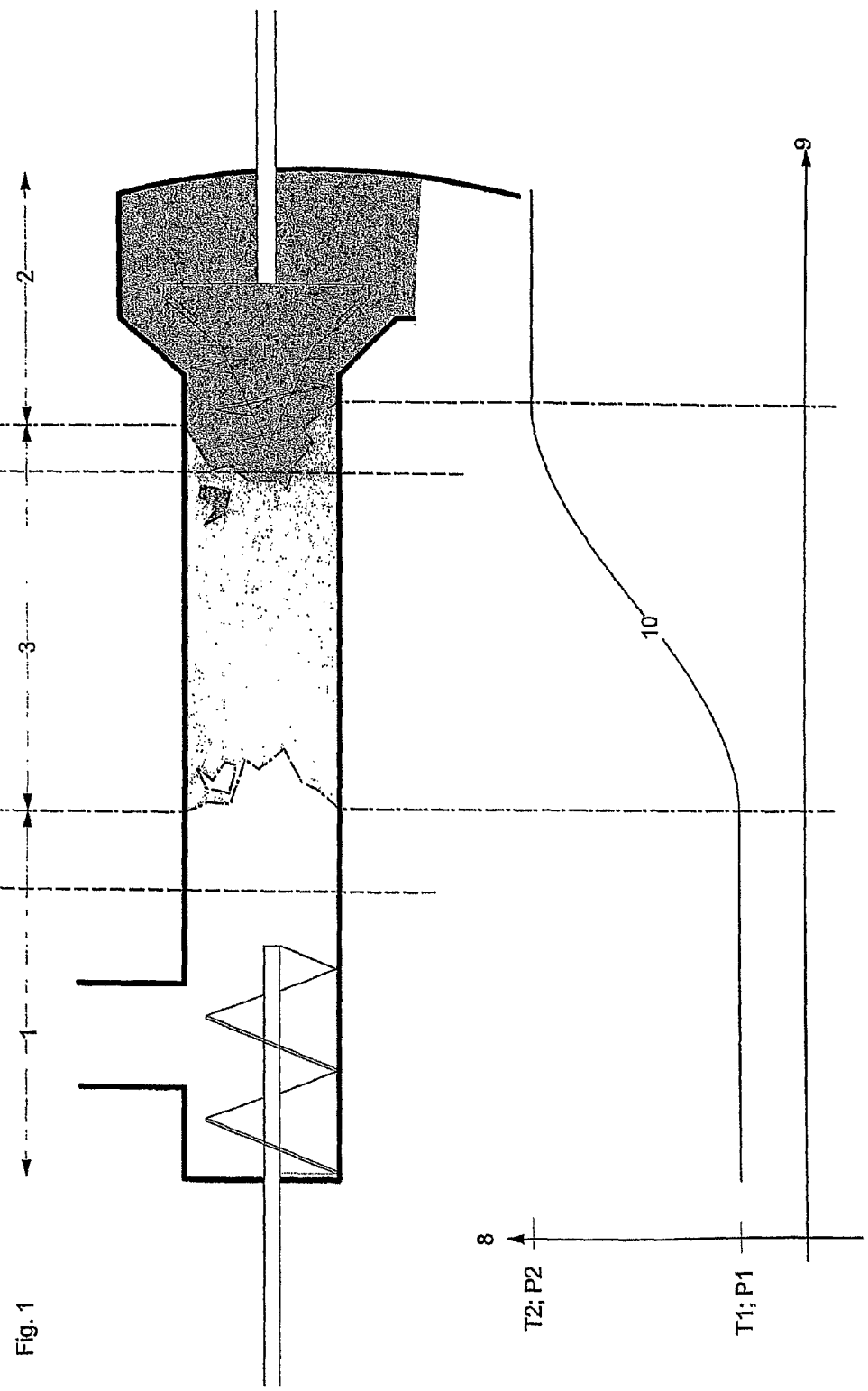

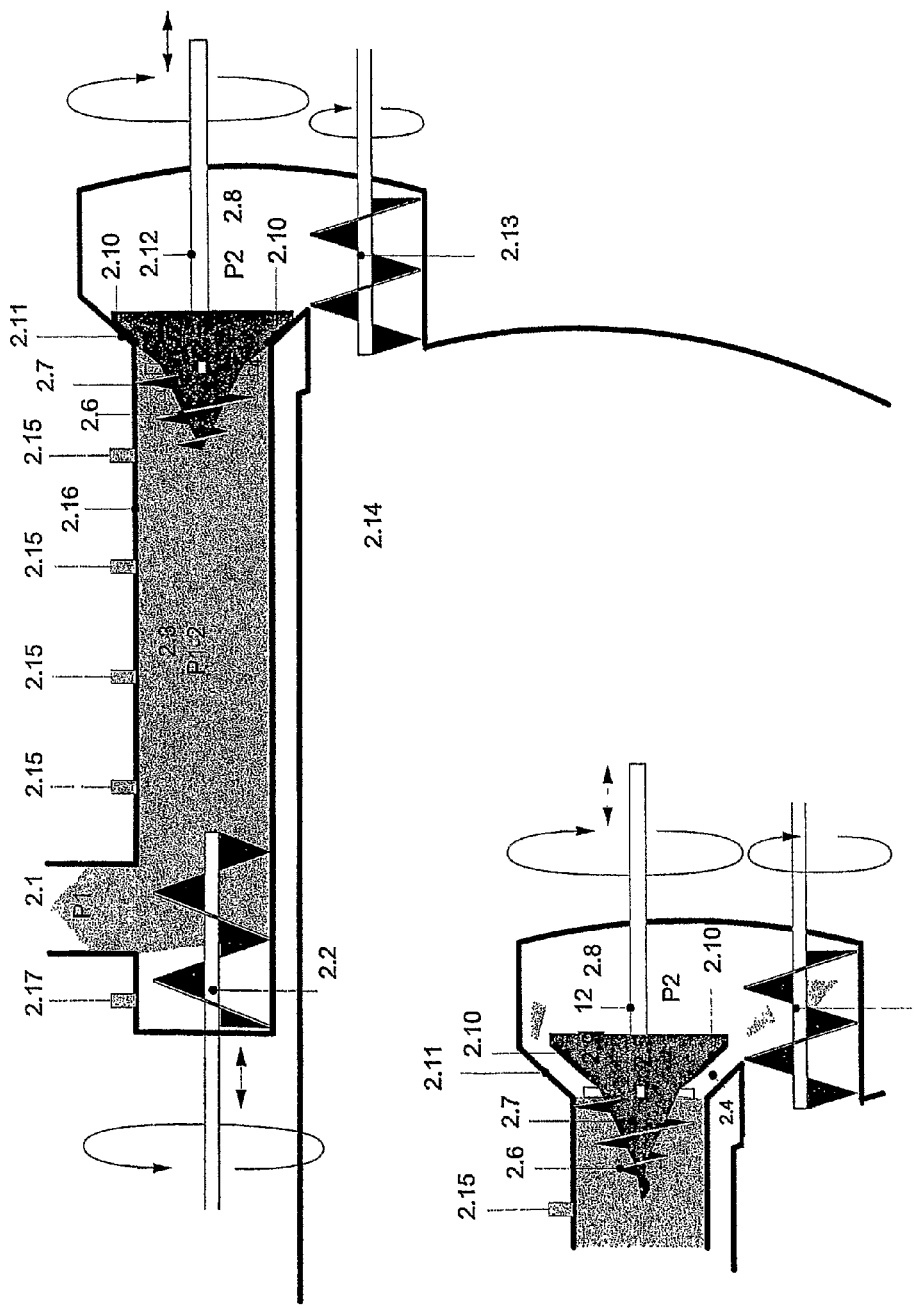

METHODS AND DEVICES FOR CONTINUOUS TRANSFER OF PARTICULATE AND/OR FIBROUS MATERIAL BETWEEN TWO ZONES WITH DIFFERENT TEMPERATURES AND PRESSURES

FIELD OF INVENTION

The invention relates in general to methods and devices for continuous transfer of particulate and/or fibrous material from a zone 1 with a low temperature T1 and a low pressure P1 into a zone 2 having a higher temperature T2 and a higher pressure P2. In particular, the invention relates to optionally continuous transfer of particulate and/or fibrous material into reactors (zone 2), wherein P2 derives primarily from vapour, which will condense at T1.

BACKGROUND

Devices for transfer of particulate and/or fibrous material into pressurized reactors are of interest in conversion of lignocellulosic biomass such as straw, grasses, corn stover, bagasse and waste wood to bioethanol and/or other useful products.

In order to provide hydrothermal pre-treatment of lignocellulosic biomass at the scale of commercial bioethanol production, throughput of 10-40 tons/hour will often be required through reactors pressurized to 10-40 bar. To achieve these high levels of "feeding" capacity, devices capable of continuous transfer of feedstocks from low pressure into pressurized reactors will be desirable.

In order to reduce energy consumption of hydrothermal pretreatment processes, it is advantageous to maintain low water content, that is, to process feedstocks at a high dry matter concentration. For hydrothermal pre-treatment of lignocellulosic biomass, more than 15% dry matter is usually considered a high dry matter content, with 30-45% dry matter as a preferred range.

The very low specific density of most lignocellulosic biomass (around 50 kg/m3 for chopped wheat straw and corn stover) makes compaction of the feedstock during feeding advantageous. Many particulate and for fibrous materials, such as straw, bagasse and household waste, also require force-loading because they have poor flow qualities, and are inclined to form bridges.

One attractive solution for transfer of particulate and/or fibrous materials into pressurized reactors is the "plug feeder." Plug feeders use loading devices to compact particulate and/or fibrous material to a high density "plug" that provides a pressure seal, because it can not be penetrated by gasses. Plug feeders can work continuously at high dry matter concentration and further provide force-loading of materials into the reactor. The density necessary to provide sufficient sealing properties of the plug may vary depending on the feedstock and the moisture content. With cereal straw, plug densities typically correspond to a specific density of 700-1100 kg solid dry matter per m3.

The plug feeder art faces several challenges that are the subject of continuing innovation. One challenge is to provide a plug having sufficient sealing properties to provide a secure barrier to the high reactor pressure. Another challenge is to avoid wear, caused by friction from the high density plug. This problem is especially great with plugs formed from particulate and/or fibrous material having a high silica content, such as rice straw, wheat straw and corn stover. Another challenge is the safety of pressure sealing in commercial scale operations. Even if a plug is normally sufficiently pressure tight, heterogeneity of feedstock material may from time to time result in formation of channels with inferior sealing properties. This can cause an explosion-like situation, when pressure in the reactor is suddenly released. This not only causes a production stop, but is potentially dangerous to personnel. Another challenge is the requirement for disintegration of the plug at the entrance to the high pressure reactor. Still another challenge is the general requirement to minimize energy consumption and processing steps. Friction between the high density plug and the feeding equipment may also cause such high temperatures that the feedstock is thermally degraded, and therefore less suited for further treatment.

In the prior art, the primary challenge of pressure sealing has generally been addressed by increasing plug density (ref 5) or by trying to prevent negative effects of high plug density (ref 3). These "high density" solutions have disadvantages, however. High density plug feeders often require mechanical degradation (particle size reduction) of feedstocks in order to produce a plug that is gas impenetrable. Particle size reduction requires additional process steps and high energy consumption. High density plugs also introduce greater wear on machinery and require greater efforts at disintegration. High density plugs also result in higher energy consumption in that these require a greater degree of compaction and compensation for friction against the walls and other parts of the feeder. High density plugs also require more extensive disintegration at the reactor inlet, sometimes under harsh conditions. Moreover, plug density is only an indirect measurement of pressure sealing properties. One plug can have good sealing properties at low density and another plug can have bad sealing properties at high density.

Here we describe a new, "low density" approach to feeder methods and devices that provide transfer of a particulate and/or fibrous material from a zone 1 with a lower temperature and pressure into a zone 2 with a higher temperature and pressure. Vapour is allowed to penetrate into a comparatively low density plug in a controlled manner. Vapour condensation in the compacted feedstock eliminates leakage of vapour from zone 2 to zone 1. Embodiments of methods and devices that utilize this new approach are referred to as "flow feeders." Flow feeder methods and devices described here provide general advantages of reduced wear, reduced energy consumption and reduced need for plug disintegration at the inlet to zone 2. In many cases, plug disintegration is not necessary at all. Preferred embodiments provide improved operational safety, improved capacity to work with heterogeneous feedstocks, and improved capacity to work with feedstocks having long particles, such as straws and grasses, or large particles, such as household waste.

SUMMARY

Methods and devices are provided for optionally continuous transfer of particulate and/or fibrous material from a zone 1 with low temperature and pressure (T1, P1) into a zone 2 with a higher temperature and pressure (T2,P2) wherein the transfer is carried out by forming a flow of compacted feedstock moving from zone 1 to zone 2.

Plug feeders of the prior art provide a pressure lock between high pressure (zone 2) and low pressure (zone 1) by utilizing a high density plug, which is impenetrable by vapours and gasses. In contrast, the flow feeder methods and devices provided here utilize low density plugs that are penetrable by vapours and gasses. Leakage of condensable vapours from zone 2 to zone 1 is avoided by condensation of condensable vapours inside the compacted feedstock. Condensation occurs because feedstock in the lower pressure zone 1 has a lower temperature T1 than the condensation temperature of the vapours from the high pressure zone 2. Condensation occurs inside the compacted, moving feedstock in a condensation zone which separates zone 1 and zone 2. A condensation front defines the border between the condensation zone and zone 1.

Preferred embodiments provide a steady state operation, whereby the location of the condensation front in the flow feeder is almost stationary—the condensation front moves into the feedstock from zone 2 towards zone 1 at the same rate (velocity) at which the vapour-penetrable feedstock is moved from zone 1 towards zone 2.

Condensation of high temperature vapour from zone 2 will impart heat energy to an amount of feedstock having sufficient "heat capacity" to absorb it. If, suddenly, additional vapour penetrates into the feedstock, the condensation front will move closer to zone1 because additional feedstock ("heat capacity") is needed to absorb energy released by condensation of the additional vapour.

To avoid potentially explosive leakage of vapour to zone 1, preferred embodiments monitor the location of the condensation front. If the condensation front moves too far towards zone 1, a variety of different means can be used to re-establish the condensation front safely within the flow of compacted feedstock.

BRIEF DESCRIPTION OF THE FIGURES

FIG. 1 shows a schematically longitudinal section illustrating principles of operation of one embodiment of a flow feeder.

FIG. 2 A shows a longitudinal section view of a preferred embodiment wherein the unloading device is closed for start-up or for emergency reasons FIG. 2 B shows a section of the preferred embodiment shown in 2A, wherein the unloading device is open for steady-state operation.

DETAILED DESCRIPTION OF PREFERRED EMBODIMENTS

Flow feeder methods and devices are provided for optionally continuous transfer of particulate and/or fibrous material from a zone 1 with low temperature and pressure (T1, P1) into a zone 2 with a higher temperature and pressure (T2,P2). In preferred embodiments, the transfer is accomplished by a device that forms a continuous flow of compacted feedstock moving from zone 1 to zone 2.

Preferred embodiments provide continuous feeding of particulate and/or fibrous material into a pressurised reactor at lower cost, with lower energy consumption, reduced wear and a high level of operational safety.

These and other advantages are provided using a new approach to the function of the feedstock as pressure barrier. Plug feeders of the prior art rely on vapour-impenetrable, high density plugs to provide a pressure lock between the high pressure zone and the low pressure zone. In contrast, the flow feeder methods and devices provided work with low density, vapour-penetrable plugs. Condensation of vapours inside the flow of compacted feedstock avoids leakage of condensable vapours from zone 2 to zone 1.

The term "vapour" as used here refers to gasses which will condense at T1. The term "gasses" as used here refers to gasses which will not condense at T1.

Gasses from zone 2 with condensation temperatures lower than T1, will move through the compacted, vapour-penetrable feedstock towards zone 1. Air contained in the feedstock will be driven out at the condensation front and remain in zone 1. Accordingly, In preferred embodiments, the vapour-penetrable plug will allow gasses from zone 2 which do not condense at T1 to be removed with a very low loss of energy.

Condensation of vapours inside the flow of compacted feedstock occurs because feedstock in the lower pressure zone 1 has a lower temperature T1 than the condensation temperature of the vapours from the high pressure zone 2. Condensation occurs inside the compacted, moving feedstock in a condensation zone in the flow feeder chamber.

The flow feeder chamber is the chamber bounded on the inlet, zone 1 end by the loading device and at the outlet, zone 2 end by the unloading device. The condensation zone is the section of the flow feeder chamber where condensation occurs beginning close to the outlet, zone 2 end and ending at the condensation front. The term "condensation front" as used here refers to the interface between the condensation zone and zone 1 which forms in the flow feeder chamber.

A "condensation front" covers the cross section of the flow feeder chamber, but can have irregular shape.

The term "condensation front velocity" refers to the rate at which the condensation front moves into compacted feedstock material in the direction P2 to P1. In preferred embodiments of the invention where compacted feedstock material is itself moving in the direction P1 to P2, at the same rate as the condensation front velocity in the direction P2 to P1, the position of the condensation front in the flow feeder chamber is stationary, notwithstanding a non-zero value of condensation front velocity.

The term "heat capacity" as used here refers to the capacity of a given volume of feedstock to absorb high temperature steam as condensed water. The initial moisture content will affect the "heat capacity."

In preferred embodiments, the continuous flow of feedstock from zone 1 has sufficient "heat capacity" to ensure complete condensation of all vapour penetrating into the feedstock from zone 2.

In preferred embodiments a steady state operation is established, whereby the location of the condensation front in the flow feeder is relatively constant because it moves into the feedstock from zone 2 towards zone 1 at the same rate (velocity) at which the penetrable/condensating plug is moved from zone 1 towards zone 2.

Velocity of the condensation front is controllable. The term "controlled velocity" as used here refers to a method in which significant vapour penetration of the moving feedstock plug is intended and in which the rate of movement of the condensation front into the moving plug is intentionally exploited.

Velocity of the condensation front into the compacted feedstock can be detected by monitoring systems based on sensors well known in the art such as thermo- and pressure sensors, thermographic detection or sensors detecting the increased water content in the condensation zone. Also, expansion of the flow feeder chamber at the condensation zone can be used to detect location of the condensation front. In preferred embodiments, sensors inform a feed back system that controls velocity of the condensation front, for example, by controlling plug compaction through control of the feedstock loading or unloading rate.

In preferred embodiments, velocity of the condensation front into the feedstock plug in the direction from zone 2 to zone 1 is adjusted to equal the velocity of the feedstock itself in the direction zone 1 to zone 2. In this manner, steady-state conditions are achieved, where the location of the condensation front does not move in relation to the flow feeder chamber. This provides a pressure seal, avoiding leakage of vapour from zone 2 to zone 1. Operating in steady-state conditions, methods of the invention will be practiced in an essentially continuous manner. The term "continuous" as used herein refers to conditions in which the flow of feedstock is substantially not interrupted by particle free spaces and without stopping the movement of the feedstock plug, except for production stop or emergency situations.

When the condensation front moves too far towards zone 1, the risk is increased for an explosive release of huge amounts of steam into the surroundings.

Steady state operation can be maintained in the flow feeder by initiating counteracting precautions if the condensation front moves towards zone 1 or 2. Counteracting precautions to maintain steady state operation can aim at adjusting the flow of heat energy, by adjusting the flow of vapour. Alternatively, the adjustments can aim at adjusting the capacity of the flow of feedstock to absorb energy. In practicing some embodiments, adjustments can affect both the vapour penetration rate and the capacity to absorb energy as e.g. adjusting the compaction, since a higher density can both decrease the vapour penetration rate and increase the capacity to absorb energy.

When the condensation front moves closer to zone 2, the flow of vapour energy into the feedstock plug is lower than the energy absorption of the feedstock plug moving counter currently. As the condensation front approaches the reactor inlet end of the compaction zone, the loading device is effectively forcing compacted feedstock plug against the high pressure of zone 2. Under these conditions, energy consumption of the loading device will increase strongly, approaching energy consumption of a prior art high density plug feeder.

The feedstock is typically compacted to a comparatively lower density at which vapour from a high pressure reactor can penetrate at a controlled velocity into the feedstock, moving in the direction towards the lower pressure feedstock inlet (zone 1).

Flow feeder methods and devices of the invention can operate effectively at levels of plug density much lower than have been achieved using plug feeders of the prior art. For example, loading against a reactor pressure of >10 bar, specifically 15 bar, flow feeder methods may be practiced using any suitable feedstock including cereal straw, bagasse, corn stover, corn cobs, wood chips, empty fruit bunches and other feedstocks compacted to densities much lower than 700 kg/m3, typically within the range of 200-400 kg/m3, optionally lower than 320 kg/m3, lower than 300 kg/m3 or even lower than 215 kg/m3.

The vapour from the high pressure reactor (zone 2) will condense within the vapour-penetrable, compacted feedstock plug, forming a condensation zone and a corresponding condensation front. The temperature and pressure of feedstock within the condensation zone will increase from T1 and P1 towards T2 and P2. The condensation front moves within the vapour-penetrable feedstock plug in the direction from zone 2 towards the zone 1. This motion of the condensation front is counter-current to the motion of the feedstock plug itself, which is moving in the direction from zone 1 towards zone 2.

In preferred embodiments, the plug is compacted to a length that is sufficiently long to prevent channeling from zone 2 to zone 1 and to provide sufficient time to take suitable precautions if the condensation front starts to move towards zone 1.

The methods of the invention are particularly well suited for loading reactors for hydrothermal pre-treatment of lignocellulosic biomass with or without catalysts such as acids, bases or oxygen.

Any suitable feedstock may be used to practice methods of the invention. As used here the term "feedstock" refers to material of biological origin, including materials derived from plants, animals and fungus, including processed materials such as paper, textile, restaurant and household waste or fractions thereof.

A variety of means can provide compaction of feedstock to form a moving feedstock flow having a suitable density at which vapour from zone 2 can penetrate, forming a condensation front that moves at a controllable velocity towards zone 1. In preferred embodiments, a loading device compacts feedstock within the confines of a flow feeder chamber against a variable counter-pressure. Variable counter-pressure can be provided by a variety of different means including an unloading device or a choke member, which can also close the outlet of the flow feeder completely in emergency and start-up situations.

A suitable loading device may be, for example, a screw conveyor or a piston screw conveyor that moves the feedstock in the direction from zone 1 towards zone 2, against a counter pressure.

A suitable unloading device may comprise a disc or other plug-contact face having an outlet-contact face, the outlet having a corresponding contact face surrounding the outlet from the flow feeder chamber, the disc mounted on a shaft by which the disc or plug-contact face can be rotated or moved axially. In preferred embodiments, an unloading device may also serve as a pressure-lock and/or a plug disintegration device as described in ref. 1 and 2. An unloading device can provide counter pressure because the area open to feedstock passage past the unloading device can be adjusted to be less than the cross sectional area of the flow feeder chamber. The area open to feedstock passage can be adjusted by the axial movement of the unloading device. When the unloading device is moved toward the inlet the area is decreased and the counter pressure is increased, which increases plug density. When the unloading device is moved away from the inlet, the area is increased, and counter pressure and plug density decreased.

Alternatively, the counter pressure may be provided by devices lacking an active unloading function but having modified features of known plug feeders used to operate at higher plug densities. For example, counter pressure may be provided against an outlet having a variable aperture or a choke member, such as the device described in ref. 3 and 4. In preferred embodiments the choke member comprises several moving parts, and can act as a pressure lock during start up procedure and in emergency situations.

Velocity of the condensation front into the compacted feedstock plug can be adjusted by a variety of means. Adjusting the compaction of the feedstock plug serves to adjust both the flow of vapour energy entering into the feedstock and also the "heat capacity" of the feedstock flow. Increased compaction will lead to decreased flow of vapour energy and it will also lead to increased "heat capacity." Compaction can be adjusted by a variety of means such as by increasing the loading rate in a short period, which is repeated until the desired density has been achieved; or by decreasing the unloading rate in a short period, which is repeated until the correct compaction has been achieved. The compaction can be for example decreased by decreasing the loading rate in a short period, which is repeated until the correct density has been achieved; or by increasing the unloading rate in a short period, which is repeated until the correct density has been achieved.

Adjusting the moisture content of the feedstock can also serve to adjust the velocity of the condensation front. The moisture content of the feedstock contributes substantially to the "heat capacity" of the feedstock. Higher moisture content can reduce vapour penetration by making the feedstock more flexible and compressible. Moisture content may also provide gelation and/or swelling of some feedstock constituents, thereby increasing vapour penetration resistance.

In preferred embodiments, where methods of the invention are practiced to load lignocellulosic feedstocks into hydrothermal pre-treatment reactors, the preferred moisture content of the feedstock is normally 40-80% (20-60% dry matter) and more preferred between 55-70% (30-45% dry matter). This range facilitates establishing and maintaining steady state operation.

The moisture content of feedstock like wheat straw, corn stover and saw dust is normally too low (10-40%) for an effective hydrothermal pre-treatment process and will also require high compaction to establish.

By increasing the moisture content of these dry biomasses to a range of 55-70% before they enter into a low density plug feeder, optimal conditions will be established for both the flow feeder and the pre-treatment process.

Some materials like e.g. silage usually have favourable moisture content, and may be loaded into the flow feeder without previous treatment. If the material has higher moisture content than desired, it can be reduced by pressing prior to loading.

Adjusting the particle size and/or shape of the feedstock can also serve to adjust the velocity of the condensation front. Feedstock particles can have many different shapes and sizes. The shapes can be divided into three groups:

Long particles. One dimension is dominating, meaning the particles are substantially larger in one dimension than in the two other dimensions, e.g. straw, corn stover, bagasse, and grasses.

Flat particles. Two dimensions are dominating, meaning the particles are substantially larger in two dimensions than in the third dimension, e.g. leaves, paper, wood shavings.

Lumpy particles. No dimension is dominating, meaning the particles are approximately equally large in all three dimensions, e.g. wood chips.

Vapour penetration into the feedstock plug will be reduced if the long and/or flat particles are placed in such manner that the dominating direction of elongated or flat particles is perpendicular to the direction in which the compacted feedstock moves. Such preferential placement of particles may be achieved using a variety of means such as using a screw or a screw piston as the forwarding means, the edge of the last screw blade will arrange elongated and flat particles in the desired direction. This mechanism is probably enhanced by favourable moisture content, because the particles are more flexible than when they are dry.

If the feedstock consists of lumpy particles such as wood chips, it may be an advantage to supply it with long or flat particles or small particles such as saw dust. As an alternative to chips waste wood could be rendered into long or flat particles to adapt it to the flow feeder.

In the past, sugar cane harvesting has typically discarded leaves, because they were considered of no value. By introducing harvesting methods such as single pass whole crop harvesting which also collects the leaves, the biomass yield will be increased, and the properties of the biomass will be enhanced in respect to provide an appropriate vapour penetration rate at lower compaction.

The flow feeder methods of the invention can be practiced using feedstocks having rather long particles. For elongated particles like straw, grasses or corn stover, a flow feeder of industrial size will easily accept particles as long as 20 cm.

If a lower condensation front velocity is desired, it is normally an advantage that the flow feeder receives a mixture of small and large particles, since the small particles will seal the spaces between the large particles, thereby decreasing the vapour penetration rate. Many feedstock materials contain a variety of particle sizes. It may also be advantageous to mechanically degrade a portion of the material and mix it with large particles. Or it may be advantageous to mix two different feedstock materials, one with larger particles and one with smaller particles.

A valuable advantage provided by some embodiments is reduced consumption of electricity by the loading device, because no energy is required to force the feedstock against the pressure P2, when the compacted feedstock is penetrable and the vapour completely condensed in the flow feeder chamber, in contrast to a traditional plug feeder relying on an impenetrable plug, where the loading device must compensate for the pressure P2 on the end surface of the plug as well as it must compensate for friction between plug and equipment.

Methods of the invention can also provide a variety of other possible advantages. The use of comparatively lower compaction of the feedstock reduces energy consumption and also the need for feedstock disintegration at the entrance to the reactor is reduced. The reduced requirement for particle size reduction by the flow feeder will also provide energy savings. The feedstock for hydrothermal pre-treatment will achieve the reactor temperature prior to actually entering the reactor, thereby decreasing retention times in the reactor. Overall efficiency of hydrothermal pre-treatment can also be improved in that vapour penetration into the feedstock will effectively drive air out from cells, capillaries and other cavities in the feedstock, thereby securing improved contact between the intracellular surfaces of the feedstock and the vapour in the reactor.

Some preferred embodiments of an apparatus of the invention, suitable for practicing methods of the invention, comprise:

A cylindrical flow feeder chamber with an inlet opening in the cylindrical wall for loading the plug material into the plug chamber from zone 1 with the temperature T1 and the pressure P1, and an open end for unloading the feedstock into zone 2 with the temperature T2 and the pressure P2

A loading device that is situated so as to be loaded with feedstock through an inlet opening An unloading device providing adjustable counter pressure A discharge zone around the unloading device, where it is possible to create a pressure lock.

Optionally further comprising a device for force-loading the product into a pressurized reactor.

Preferred embodiments are adapted to conduct a continuous flow of compacted feedstock from zone 1 to zone 2. A screw conveyor is a good and inexpensive loading device but at high counter pressure, the plug may rotate, causing the forward movement of the plug to stop.

A piston screw is technically more complicated as loading device than a screw conveyor, but it secures the forward movement of the product. Both solutions will strongly reduce the risk of formation channels in the compacted feedstock. Other conveyor systems could also be used to provide a loading device.

In some preferred embodiments, counter pressure, adjustment of plug density, disintegration of the plug, prevention of plug rotation and pressure lock for emergency and start up situations, are all provided by a single unloading device. This unloading device can also be designed to force unload the plug. A preferred embodiment of such an unloading device comprises:

A disc with a plug-contact face and an additional contact face surrounding the outlet from the flow feeder chamber A shaft by which the disc can be moved axially and rotated A cork screw with the free end removing the feedstock from the penetrable plug.

The unloading device can provide a variable counter pressure for the motion of the low density plug by regulating rotation of the unloading device. Slow rotation provides increased compaction and vice versa. The area open to feedstock passage can be adjusted by axial movement of the unloading device.

In emergency situations where there is a risk of severe leakage or during start up procedures, the disc can be closed entirely against the contact face of the outlet, thus providing a pressure lock.

In situations where there is a growing risk of leakage, it will often be sufficient to move the unloading device towards the outlet, without closing it entirely. This will create an annular compaction zone between the contact face of the unloading device and the corresponding contact face of the outlet, which has a higher vapour penetration resistance than the main compaction zone. After a short time, the compaction of the feedstock in the main compaction zone will increase, and the sufficient vapour penetration resistance and condensation capacity can be restored, and the unloading device will be moved away from the outlet again.

The term "cork screw" refers to a screw which has a shaft in one end, and no shaft in the other pointed end, (in the following called the free end). The inventive cork screw uses the free end to remove the feedstock from the compaction zone, and will move it in the direction of the shaft.

In order to avoid rotation of the compacted feedstock, the unloading device can rotate in the opposite direction of the loading device.

Operational safety can be improved in some embodiments by providing a vapour safety outlet, which can transmit vapour in a controlled manner e.g. to a condensation unit, or to the environment, until steady state operation has been re-established.

Safety can be further improved by operating two flow feeders in series. The temperature and pressure in the discharge zone of the first flow feeder will be around the middle between T1 and T2 and P1 and P2 The safety will be improved by two flow feeders of the following reasons:

The pressure difference is reduced for each flow feeder.

There can be two pressure locks, which can close in emergency situations

The discharge/loading zone between the two flow feeders is a good place to make the pressure measurements, which can detect leakage of vapour from zone 2 immediately and start the counteracting precautions.

Accordingly, in some preferred embodiments, the apparatus of the inventions comprises a cylindrical flow feeder chamber having an inlet opening for loading said feedstock from a zone 1 with a temperature T1 and a pressure P1, and having an open unloading end connected to a zone 2 with a temperature T2 and a pressure P2, a screw conveyor or piston screw conveyor that is situated so as to be loaded at the shaft end with said feedstock through the inlet opening, and to load said feedstock into the flow feeder chamber at the free end.

an axially movable unloading device situated at the unloading end of the flow feeder chamber having, at the outlet side outside the flow feeder chamber, a cone with a larger diameter than that of the flow feeder chamber, and equipped with a ring-shaped contact area in the periphery outside the flow feeder chamber, and a discharge chamber, providing a pressure tight connection between the flow feeder chamber and the reactor with pressure P2, in which the wall connecting to the flow feeder chamber includes a ring shaped contact area adapted to contact the contact surface on the unloading device, and which permits establishment of a pressure lock between the flow feeder chamber and the discharge chamber by closing the gap between the two contact areas.

FIG. 1 shows a schematically longitudinal section illustrating principles of operation of one embodiment of a flow feeder.

As shown in FIG. 1, Zone 1 (1) at the inlet end of the flowfeeder has a lower temperature and pressure T1 and P1 than zone 2 (2) at the outlet end of the flow feeder, which has temperature and pressure T2 and P2. The pressure P2 mainly derives from vapours which will condense at T1. The vapours from zone 2 will penetrate into the feedstock. When the vapour passes the high pressure front (6) it will begin to condensate in the condensation zone (3) where the temperature is lower than T2 as illustrated by the curve (10) schematically showing the relation between pressure and temperature (8) and location in the flow feeder (9). Vapour which has condensed, will follow the feedstock flow, moving counter currently to the vapour penetrating the feedstock. All of the vapour penetrating from zone 2 has been condensed at the condensation front (4), because the heat absorption capacity of the feedstock flow in the condensation zone (3) equals the heat energy deriving from the vapour penetrating and condensing in the feedstock flow.

The area (5) is an approximate boundary between relatively less compacted feedstock and feedstock that has been relatively more compacted by counter pressure of the loading device against the unloading device. The area (7) is an approximate boundary between relatively compacted feedstock and feedstock that is relatively less compacted due to action of the unloading device.

EXAMPLE

One preferred embodiment of an apparatus of the invention and its method of use according to one preferred embodiment of methods of the invention is here described in detail, referring to FIG. 2A and FIG. 2B.

FIG. 2A shows a longitudinal section view of a preferred embodiment wherein the unloading device is closed for start-up or for emergency reasons FIG. 2B shows a section of the preferred embodiment shown in 2A, wherein the unloading device is open for steady-state operation.

The feedstock is loaded into the flow feeder through the inlet 2.1. The pressure in the inlet is P1. A piston screw 2.2 is placed under the inlet 2.1. The piston screw feeds the feedstock into the flow feeder chamber 2.3 towards the outlet 2.4. The flow feeder chamber 2.3 is an elongated cylinder. During operation, the pressure in the flow feeder chamber is P1 in the inlet end and P2 in the outlet end 2.4. An unloading device 2.5 is placed in the unloading chamber 2.8. The unloading device comprises a cork screw device 2.6, mounted on a cone 2.7, a disc 2.9 with a contact face 2.10, which corresponds to a contact face 2.11, which surrounds the outlet 2.4 and a shaft 2.12 which enables the unloading device to rotate and to move axially in the unloading chamber 2.8.

During start-up procedure, the outlet 2.4 is initially closed by the unloading device 2.5. The contact face 2.10 of the disc 2.9 is in contact with the contact face 2.11 of the outlet 2.4. Feedstock is loaded into the feeder through the inlet 2.1 and is transported towards the outlet 2.4 by the piston screw 2.2. Since the outlet is closed, the flow feeder chamber 2.3 will be filled with feedstock between the inlet and the outlet. By loading further material, the feedstock is compacted to a desired value at which the condensation front velocity will reach a desired level. When the density has achieved the desired value, the unloading device is opened (FIG. 2B), rotating in the opposite direction of the piston screw. By the rotation, the cork screw 2.6 disintegrates the feedstock, and moves it through the outlet 2.4 and into the discharge chamber 2.8, where it is transported by the screw conveyor 2.13 into the reactor 2.14. The unloading device also provides adjustable counter pressure for the piston screw, to maintain the desired condensation front velocity.

The location of the condensation front is determined during operations by reference to several temperature monitors 2.15 placed along the wall 2.16 of the flow feeder chamber 2.3. These monitors identify the location of the condensation front within the flow feeder chamber 2.3. The temperature will correspond to T1 on the inlet side of the condensation front. Maintenance of the desired condensation front velocity is determined by a feed back system that is informed by these sensors.

One monitor 2.17 is placed in the empty space beside the feedstock inlet. This monitor can be a temperature and/or pressure monitor. If the pressure or the temperature rises above P1, T1 at monitor 2.17, the unloading device 2.5 will automatically close immediately. The closing mechanism of the unloading device 2.5 will close in case of power failure where the feeding and the condensation of the vapour will stop.

The examples and descriptions above provide representative examples of particular embodiments and are not intended to limit the scope of the invention as defined by the claims.

References
1. U.S. Pat. No. 3,841,465
2. U.S. Pat. No. 4,274,786
3. U.S. Pat. No. 4,947,743
4. U.S. Pat. No. 5,466,108
5. SE 500516

The invention claimed is:

1. A method for transferring particulate and/or fibrous feedstock from a zone 1 with lower temperature T1 and a lower pressure P1 into a zone 2 having a higher temperature T2 and a higher pressure P2, wherein P2 mainly derives from vapour which will condense at T1, comprising
   compaction of said feedstock in a flow feeder chamber to form a moving plug having a density at which vapour from P2 can penetrate said moving plug, forming a condensation front that moves at a controllable velocity towards P1 into said plug, counter-current to the motion of said plug which is from P1 towards P2, and
   avoiding leakage of vapour from P2 to P1 by adjusting the velocity at which said condensation front moves towards P1 into said plug relative to the velocity at which said plug moves from P1 to P2.

2. The method of claim 1 wherein the condensation front velocity is adjusted during operation in such manner that the position of the condensation front in the flow feeder chamber is stationary, thereby creating steady state operation.

3. The method of claim 1 wherein the condensation front velocity is controlled by a feed back system, optionally securing steady state operation.)

4. The method of claim 1 wherein compaction of said feedstock to form a moving penetrable plug is provided by a loading device working against a counter-pressure provided by a choke member, by which the counter pressure and thereby the compaction and thereby the vapour penetration rate can be adjusted during operation.

5. The method of claim 1 wherein compaction of said feedstock to form a moving plug is provided by a loading device working against counter-pressure provided by an unloading device, by which the counter pressure and thereby the compaction and thereby the vapour penetration rate can be adjusted during operation.

6. A method according to claim 5, wherein the unloading device is an axially movable conical screw conveyor with a conical body having a pointed free end penetrating into the compacted feedstock and an opposite end being the shaft end of the conical body and having a larger diameter than the flow feeder chamber through which the plug is moving, said flow feeder chamber being equipped with a funnel shaped outlet, whereby the counter pressure can be adjusted by axial displacement of the unloading device, which will regulate out-flow area.

7. A method according to claim 5 wherein the unloading device is a cork screw with a pointed free end penetrating into the plug and an opposite shaft end equipped with a driving means, whereby the counter pressure can be adjusted during operation by regulating the speed of rotation.

8. A method according to claim 5, wherein the unloading device is used to provide a pressure lock between zone 1 and zone 2 in up-start and emergency situations.

9. A method according to claim 4 wherein the choke member is used to provide a pressure lock between zone 1 and zone 2 in up-start and emergency situations.

10. The method of claim 3 conducted under conditions in which location of the condensation front is monitored using sensors.

11. The method of claim 10 wherein said sensors are temperature and/or pressure sensors placed in a cylindrical wall defining the flow feeder chamber.

12. A method according to claim 3 conducted under conditions in which location of the condensation front is monitored using thermography.

13. A method according to claim 3 wherein the power consumption of the loading device is monitored, and used for feedback purposes.

14. A method according to claim 1 wherein compaction of feedstock is provided by a screw or piston screw receiving the feedstock close to a shaft end and delivering it to opposite free end.

15. A method according to claim 1 wherein the condensation front velocity is adjusted by adjusting the compaction of the feedstock.

16. A method according to claim 15 wherein the condensation front velocity is decreased by increasing loading rate or decreasing unloading rate.

17. A method according to claim 15, wherein the condensation front velocity is increased by decreasing loading rate or increasing unloading rate.

18. A method according to claim 1 wherein the condensation front velocity is adjusted by adjusting moisture content of the feedstock.

19. A method according to claim 18 wherein the moisture content of straw, corn stover being dry feedstock is increased upstream by soaking the dry feedstock in a liquid fraction deriving from mechanical dewatering of pretreated feedstock.

20. A method according to claim 19, wherein the moisture content of a feedstock soaked in a liquid is decreased by mechanical dewatering before or during compaction.

21. A method according to claim 18 wherein the moisture content of fresh grass, silage of grass, silage of bagasse being wet feedstock is decreased by mechanical dewatering before compaction.

22. A method according to claim 1 wherein the condensation front velocity into the compacted feedstock is adjusted by providing the feedstock with a mixture of particles with different sizes and shapes.

23. A method according to claim 22 wherein an optimal mixture of particles is achieved by recycling a portion of pre-treated biomass.)

24. A method according to claim 22 wherein an optimal mixture of particles in the compacted feedstock is achieved by addition of a mixture of feedstocks having complementary particle sizes and shapes.

25. An apparatus for transferring particulate and/or fibrous feedstock from a zone 1 with a lower temperature T1 and a lower pressure P1 into a zone 2 having a higher temperature T2 and a higher pressure P2, wherein P2 derives primarily from vapour which will condense at T1, adapted to conduct the transfer by forming a continuous flow of compacted feedstock moving from zone 1 to zone 2, said apparatus comprising
- a cylindrical flow feeder chamber defined by a wall and having an inlet opening for loading said feedstock from zone 1, and an outlet at an open unloading end connected to zone 2
  - a loading device being a screw or a piston screw, that is situated so as to be loaded with said feedstock through the inlet opening, for loading said feedstock into the flow feeder chamber, said screw having a length and receiving the feedstock close to a shaft end thereof and delivering it at an opposite free end thereof, the distance between a last screw blade of the loading device and the outlet of the flow feeder chamber being longer than the length of the screw of said loading device,
- an axially movable unloading device situated at the unloading end of the flow feeder chamber,
- several sensors placed along the wall of the flow feeder chamber for monitoring pressure and/or temperature and
- a discharge chamber, which can be sealed in a pressure tight connection between the flow feeder chamber and zone 2.

26. An apparatus according to claim 25, wherein the unloading device comprises a conical cork screw with a cone having a free end for extending into the compacted feedstock and a shaft end outside the flow feeder chamber and being equipped with a ringshaped contact face at the periphery.

27. An apparatus according to claim 25, wherein the ring shaped contact face is adapted to contact an additional contact face surrounding the outlet from the flow feeder chamber in order to provide a pressure tight connection between the flow feeder chamber and zone 2.

28. An apparatus according to claim 25, wherein the feedstock is transferred from the discharge chamber by a second flow feeder, and the pressure in the discharge chamber is between P1 and P2.

29. An apparatus according to claim 28, wherein the transfer out of the discharge chamber is carried out in the opposite direction of the transfer into the discharge chamber.

30. An apparatus according to claim 25, wherein the feedstock is transferred from the discharge chamber to a reactor by a screw conveyor.

* * * * *